United States Patent [19]

Dusek et al.

[11] 4,306,679
[45] Dec. 22, 1981

[54] DISPENSER FOR VOLATILIZABLE SUBSTANCES

[75] Inventors: Russell L. Dusek, Armonk; Gordon R. Perry, New York; Gunther H. Bartsch, Elmont, all of N.Y.

[73] Assignee: The Drackett Company, Cincinnati, Ohio

[21] Appl. No.: 174,326

[22] Filed: Aug. 1, 1980

[51] Int. Cl.³ .............................................. A24F 25/00
[52] U.S. Cl. ....................................................... 239/59
[58] Field of Search ....................... 239/59, 58, 60, 53, 239/34, 54, 55, 56, 57; 222/187, 215, 519; 215/332, 329

[56] References Cited

U.S. PATENT DOCUMENTS

| | | |
|---|---|---|
| 1,239,584 | 9/1917 | Frank . |
| 1,589,215 | 6/1926 | Ordway . |
| 2,555,047 | 5/1951 | Logue . |
| 2,620,095 | 12/1952 | Buchan ................................ 222/215 |
| 2,657,090 | 10/1953 | Meek ..................................... 239/59 |
| 3,162,361 | 12/1964 | Palmer et al. . |
| 3,412,907 | 11/1968 | Faso ..................................... 222/187 |
| 3,804,331 | 4/1974 | Levey ................................... 239/59 |
| 4,014,501 | 3/1977 | Bukenmayer ......................... 239/58 |
| 4,051,981 | 10/1977 | Mandlak . |

*Primary Examiner*—James B. Marbert
*Attorney, Agent, or Firm*—Sharon A. Blinkoff; George A. Mentis

[57] ABSTRACT

A dispenser for volatilizable materials, such as those used to freshen or deodorize air, comprising a hollow body, rotatably attached to a closure member, and having a support for the volatilizable material contained within the hollow body; said hollow body including a resiliently compressible portion, and a substantially vertical sidewall portion extending from the compressible portion, and an aperture formed in the sidewall portion; and said closure member including an interior portion and a substantially vertical sidewall having an aperture formed therein. When the closure member and the hollow body are attached to each other the sidewall of the closure member overlaps the sidewall portion of the hollow body thereby allowing their respective apertures to be brought in and out of registry to permit air to enter the dispenser and evaporate a portion of the volatilizable material.

12 Claims, 4 Drawing Figures

U.S. Patent   Dec. 22, 1981   Sheet 2 of 2   4,306,679
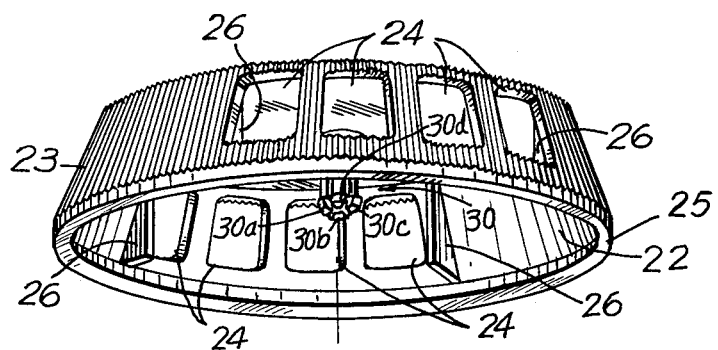
FIG. 3
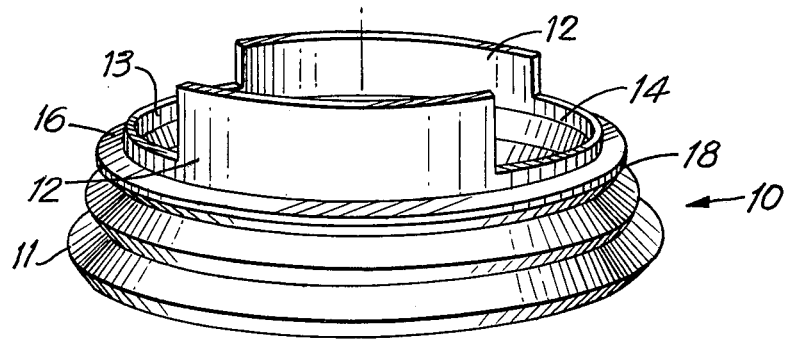
FIG. 4
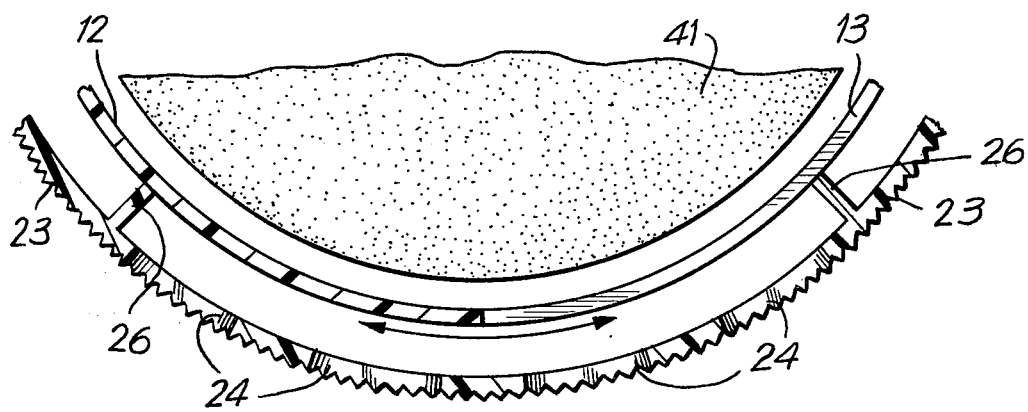

DISPENSER FOR VOLATILIZABLE SUBSTANCES

DESCRIPTION

BACKGROUND OF THE INVENTION

This invention relates to a dispenser for volatilizable substances commonly used to freshen or deodorize air. More particularly the invention relates to a dispenser having means for controlling the rate at which volatilizable substance is diffused into the atmosphere by either selectively adjusting the openings in the device to increase in size the inlet and outlet openings for the air currents or by accelerating the rate at which air passes through the dispenser by successively compressing and releasing a portion thereof.

Volatilizable substances have been commonly employed as an effective means for gradually introducing in the air a pleasing odor to deodorize or freshen air having a stale or displeasing odor. As packaged for use by consumers these materials are generally contained in dispensing devices which can be opened, either partially or completely, or closed by a simple mechanical action such as the twisting or the partial removal of the overcap.

When opened either partially or completely air currents are allowed to pass through the container thereby contacting the volatilizable substance causing the evaporation of a portion of the substance and its emission into the air surrounding the dispenser. When the dispenser is closed air is prevented from contacting and evaporating the substance, thereby preventing it from being emitted into the air. Thus by opening and closing these dispensers the consumer can control whether or not the container will emit a fragrance.

Several prior art devices permit, to a limited degree, control over the rate of emission from these containers by either limiting the surface area of the substance which is exposed to the air currents which pass through the container, or by limiting the inlet and outlet openings of the container thereby adjusting the amount of air which passes through the container. Exemplary of these types of devices are U.S. Pat. No. 4,014,501 to Buckermeyer which discloses a device comprised of a base and an overcap where the overcap is twisted up and down in relation to the base, to control the surface area of the substance exposed to the atmosphere; and U.S. Pat. No. 2,657,090 to Meek which discloses a device comprised of a base and an overcap having a series of apertures which are arranged so that either none, some or all of the apertures may be opened upon twisting, thereby controlling the amount of air allowed to contact the substance.

These devices, however, are limited in that they rely on the air currents for the emission of the volatilizable substance and have no mechanism for providing an instantaneous charge of the substance into the air. There are instances in which it is desirable to provide such an instantaneous charge of the substance into the air such as when there is a particularly strong displeasing odor as is encountered in smokefilled rooms and in kitchens. In these circumstances most consumers would resort to using aerosol deodorants or air fresheners.

A simple mechanical device which can emit a fragrance by diffusion when left open and which can provide an instantaneous charge of a fragrance was suggested in U.S. Pat. No. 3,412,907 to Faso. This patent discloses a device comprised of a pair of concave-convex discs containing a perfumed pad and having two orifices formed on opposite sides of the device. As constructed this device is necessarily limited in its size since it must be held in a certain fashion to provide a charge of fragrance, namely a finger must be placed over one orifice in order to hold it closed while compressing the device.

SUMMARY OF THE INVENTION

Accordingly it is an object of this invention to provide a dispenser of simple mechanical construction, which can provide an instantaneous charge of a volatilizable substance into the air and which also has adjustable air inlet and outlet openings that can be adjusted to provide for controlled emission of the volatilizable substance when the device is not being used to provide an instantaneous charge of the substance. It is a further object of this invention to provide a device which is capable of operating in the above discussed modes that is not inherently limited in size by virtue of its mode of operation.

The dispenser of the present invention includes a hollow body, a closure member which is rotatably attached to the hollow body and a support for containing a substantially volatilizable substance within said body. The hollow body has a circular cross section, a resiliently compressible portion, and a substantially vertical sidewall portion extending from the compressible portion where the substantially vertical sidewall portion has at least one aperture formed therein. The closure member has a circular cross section, an interior portion, and a substantially vertical sidewall which is adapted to overlap the substantially vertical sidewall portion of the hollow body when the closure member is rotatably attached to the hollow body. The closure member also has at least one aperture located on its substantially vertical sidewall at a point which corresponds to the aperture on the substantially vertical sidewall portion of the hollow body.

When the closure member is engaged on the hollow body, the respective apertures on the hollow body and on the closure member can be rotated in and out of registry. When in either partial or complete registry air currents will be permitted to enter the dispenser and evaporate a portion of the volatilizable substance thereby causing an emission of the substance into the air surrounding the dispenser. The rate of this emission can be regulated by adjusting the apertures to either partial or full registry. If a charge of the material is desired the respective apertures on the hollow body and the closure member are brought into complete registry and the resiliently compressible portion of the hollow body can be successively compressed and released thereby expelling air out and drawing it into the hollow body, the expelled air being charged with the substance and carrying it into the ambient atmosphere surrounding the dispenser.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 3 is an exploded view of the dispenser shown in FIG. 1; and

FIG. 4 is a sectional view of the dispenser shown in FIG. 1 taken along line 4—4 of FIG. 1, which shows the substantially vertical sidewall portion of the hollow body and the substantially vertical sidewall of the closure member.

DETAILED DESCRIPTION OF THE PREFERRED EMBODIMENT

Figure 1:
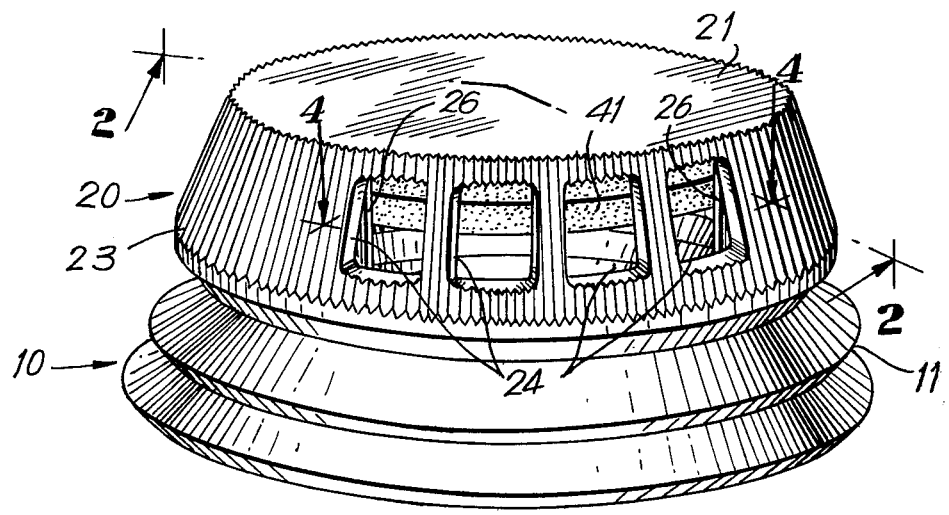
FIG. 1 is a perspective view of the preferred embodiment of the present invention.

The preferred embodiment of the present invention is illustrated by way of example in FIGS. 1-4. With specific references to FIGS. 1 and 2 the dispenser includes a hollow body 10, rotatably attached to a closure member 20, and a support 30 for containing a volatilizable substance 40.

The hollow body 10 has a resiliently compressible portion 11, and a substantially vertical sidewall portion 12 which is recessed inwardly from the resiliently compressible portion and extends upwardly therefrom. A short substantially horizontal annular wall 16 connects the substantially vertical sidewall portion 12 to the resiliently compressible portion 11. The resiliently compressible portion 11 is normally biased to an extended position and is movable to a compressed position for discharging air. As illustrated the bias is maintained by corrugated or pleated plastic in the form of a bellows where the normal strength of the plastic materials makes it resistant to compression and therefore normally biased to an extended position. As is best shown in FIG. 3 the substantially vertical sidewall portion has two large apertures 13 and 14 formed on opposite sides thereof, which divide the substantially vertical sidewall portion 12 into two segments.

Optionally the base 17 of hollow body 10 may be provided with means for attaching the dispenser to a vertical surface; such means can include for example an adhesived planar member having adhesive on both sides, suitably with the exposed adhesive surface being covered by a peelable cover sheet.

Figure 2:
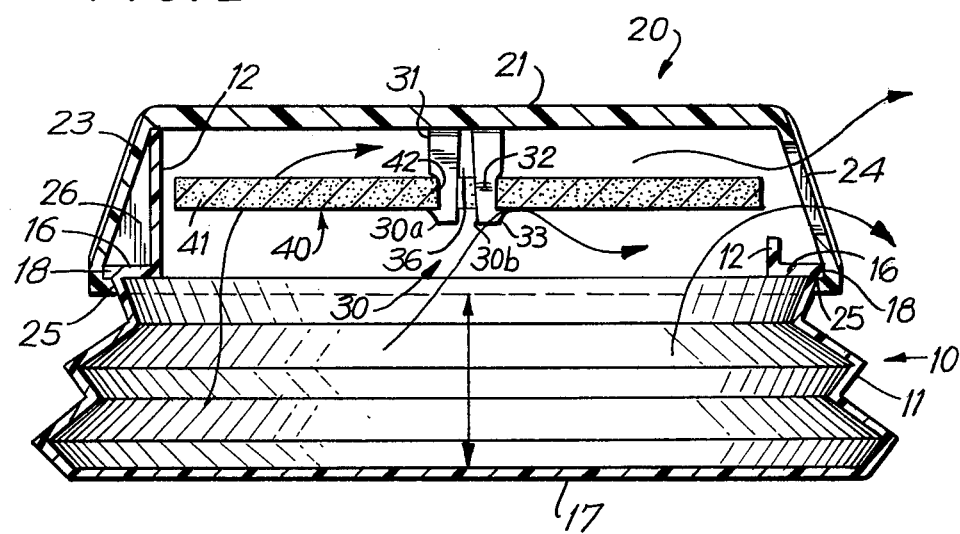
FIG. 2 is a cross-sectional view taken along line 2—2 of FIG. 1.

As shown in FIGS. 2 and 3 the closure member 20 is provided with a flat top 21, an interior surface 22, and a substantially vertical sidewall 23 which extends from top 21. A plurality of apertures 24 are formed in the substantially vertical sidewall 23, where an equal number of apertures 24 are disposed on opposite sides of substantially vertical sidewall 23. Also as shown in FIGS. 3 and 4 a plurality of fins 26 are formed along the interior of the substantially vertical sidewall 23 of the closure member 20. These fins are adapted to engage the substantially vertical sidewall portion 12 of the hollow body 10.

The means for rotatably attaching the closure member 20 to the hollow body 10, as shown in FIG. 2, includes a flange 18 which extends outwardly from annular wall 16 and an annular rib 25 which projects into the interior of closure member 20 from the bottom of the substantially vertical sidewall 23 of the closure member 20. To attach the closure member 20 to the hollow body 10 the annular rib 25 is snapped over flange 18.

The support 30 for containing the volatilizable substance 40, as shown in FIG. 2 is a post which extends into the hollow body 10 from a central portion of the interior surface 22 of the top 21 of the closure member 20. As shown in FIG. 2 the post is comprised of a first cylindrical portion 31; a second cylindrical portion 32 which is of a smaller circumference than the first cylindrical portion 31; and a frustoconical end portion 33 having a large circumference which is substantially equal to that of the first cylindrical portion 31. As is shown in FIGS. 2 and 3 the post has a series of vertical slots 36 formed therein which divide it into four segments, 30a, 30b, 30c and 30d. These slots have been included for ease of compressibility of the post for engaging the volatilizable material. As described below, the volatilizable material has a cylindrical opening formed in its central portion. When engaging the volatilizable material, the segments of the post, 30a, 30b, 30c and 30d are compressed and the volatilizable material slid up onto the second cylindrical portion 32. The compressive force on the segments of the post is then released so that the segments are permitted to return to their extended position thereby locking the volatilizable material in position.

As is shown in FIG. 2 the volatilizable material 40 includes a disc shaped layer 41 having a cylindrical opening 42 in the center thereof for engaging the support 30. The layer 41 will generally comprise a substrate impregnated and/or coated on all sides thereof with a conventional volatilizable substance. The substrate may be paper, cardboard felt, and the like, or a sponge; which materials are coated or impregnated with a volatilizable substance such as essential oils. The layer may also be a polymeric material having a fragrance entrapped therein. When the layer of volatilizable material 41 is attached to the support 30 the frustoconical end portion 33 of the support will hold layer 41 in place.

The component parts of the dispenser enumerated and described above are preferably made from plastic materials of either the polypropylene or polyethylene type. These parts can be fabricated from any of the conventional plastics and each part need not be made of the same type of material. However, the type of material used to fabricate the resiliently compressible portion of the hollow body should be capable of being compressed while being biased in the extended position. The component parts of the dispenser, the hollow body and the closure member are advantageously made by conventional molding techniques where each part is a single integrally molded member.

The dispenser of this invention is capable of being operated in two modes, it can be either partially or completely open to allow air current to enter the dispenser and evaporate a portion of the volatilizable substance and emit it to the surrounding atmosphere; or the resiliently compressible portion of the hollow body can be successively compressed and released to allow a pumping of air into and out of the dispenser thereby causing a charge of the substance to be emitted.

When used in the first mode described the emission from the dispenser can be controlled by adjusting the amount of air which enters the dispenser. This is accomplished by rotating the closure member so that the apertures on the closure member are brought into either partial or complete registry with the apertures on the hollow body.

When using the dispenser in the second mode it is advantageous to bring the respective apertures on the closure member into complete registry with the apertures on the hollow body to insure that the maximum amount of air is brought into and subsequently expelled from the dispenser while successively compressing and releasing the resiliently compressible portion of the hollow body.

When no emission of the volatilizable material is desired the apertures on the closure cap are brought into registry with the sidewall segments of the hollow body, thereby preventing air from contacting the volatilizable material. This will enable the user to stop emission when no fragrance or deodorization is desired.

While the means for rotatably connecting the hollow body to the closure member has been described and shown above to be a flange with a corresponding annular rim, any other suitable means for rotatably attaching the closure member to the hollow body can be used. Such other means for example can include mating threaded portions on the hollow body and on the closure member; or an annular groove formed on the hollow body with corresponding projections formed on the closure member, or the location of the groove and projections can be reversed.

Additionally while the support member was described above as being a post which extends into the hollow body from the interior of the closure member, the post can also project upwards from the interior base of the hollow body. Further the support member need not be a post at all, such support could be for example a cage or similar means for containing the substance which can be disposed anywhere within the hollow body either projecting up from the bottom of the hollow body or projecting down from the closure member.

Although this invention has been described by reference to the preferred embodiment, it is understood that the present disclosure has been made by way of example and that numerous changes in the details of the construction and arrangements of the parts may be resorted to without departing from the spirit and scope of this invention.

What is claimed is:

1. A dispenser comprising:
    (a) a hollow body having: A circular cross section; a resiliently compressible portion; and a substantially vertical sidewall portion extending from said resiliently compressible portion; wherein said vertical sidewall portion has at least one aperture formed therein;
    (b) a closure member having: A circular cross section; an interior surface; and a substantially vertical sidewall adapted to overlap the substantially vertical sidewall portion of said hollow body; wherein the substantially vertical sidewall of said closure member has at least one aperture formed therein at a point which corresponds to the aperture in the substantially vertical sidewall portion of said hollow body;
    (c) means for rotatably retaining said closure member on said hollow body; and
    (d) a support for containing a substantially volatilizable substance within said hollow body; whereby when the closure member is attached to the hollow body the closure member can be rotated so that the apertures on the sidewall of closure member can be brought in and out of registry with the aperture on the substantially vertical sidewall portion of the hollow body, when the respective apertures are in registry with each other the ambient air can contact the volatilizable substance and upon the compression and release of said resiliently compressible portion air can be expelled from the interior of said hollow body and drawn into said hollow body, said air being charged with and carrying to the ambient atmosphere a portion of said volatilizable substance.

2. The dispenser of claim 1 wherein said hollow body is an integrally molded piece.

3. The dispenser of claim 2 wherein said closure member has a flat top; and wherein said substantially vertical sidewall of said closure member extends downwardly from the periphery of said top.

4. The dispenser of claim 3 wherein said means for rotatably retaining the closure member on said hollow body comprises:
    (a) a flange extending outwardly from said hollow body at the point where the substantially vertical sidewall portion of said hollow body meets the resiliently compressible portion of said hollow body; and
    (b) an annular rib which projects into the interior of the closure member from the bottom of the substantially vertical sidewalls.

5. The dispenser of claim 4 wherein said support for containing a substantially volatilizable substance is a post which extends into the hollow body from the top of said closure member and wherein said post has a means for attaching said volatilizable material.

6. The dispenser of claim 5 further comprising a volatilizable substance wherein said volatilizable substance is a layer of solid substrate impregnated or coated on all sides thereof with a voltilizable material.

7. The dispenser of claim 6 further comprising a planar member which extends across the top of said resiliently compressible portion of the hollow body; and wherein said planar member has an orifice formed in a central portion thereof.

8. The dispenser of claims 6 or 7 wherein two apertures are formed on opposite sides of said substantially vertical sidewall portion of said hollow body; and wherein a plurality of apertures are formed on opposite sides of said substantially vertical sidewall of said closure member.

9. The dispenser of claim 8 wherein four apertures are formed on one side of said substantially vertical sidewall of said closure member and wherein four apertures are formed on the opposite side thereof.

10. The dispenser of claim 9 wherein the resiliently compressible portion of said hollow body is a bellows.

11. The dispenser of claim 10 wherein the substantially vertical sidewall portion of said hollow body is recessed from the top edge of the compressible portion of the hollow body; and wherein an annular wall connects the substantially vertical sidewall portion of said hollow body to the compressible portion of said hollow body.

12. The dispenser of claim 11 further comprising a plurality of fins disposed along the interior surface of said substantially vertical sidewall of said closure member.

* * * * *